United States Patent [19]

Brubaker

[11] Patent Number: 5,432,084
[45] Date of Patent: Jul. 11, 1995

[54] DEVICE FOR IN VITRO BLEEDING TIME DETERMINATION

[75] Inventor: Daniel B. Brubaker, Clovis, Calif.

[73] Assignee: Espress Tech, Inc., Clovis, Calif.

[21] Appl. No.: 216,189

[22] Filed: Mar. 22, 1994

[51] Int. Cl.⁶ .............................................. C12M 1/40
[52] U.S. Cl. ................................... 435/288; 435/291; 422/73; 422/99; 73/64.41
[58] Field of Search ................ 435/13, 287, 288, 291, 435/296, 298, 311, 809; 436/69, 165, 809; 422/58, 61, 69, 73, 101, 99, 68.1, 104; 73/64.41, 64.43

[56] References Cited

U.S. PATENT DOCUMENTS

| | | | |
|---|---|---|---|
| 3,661,717 | 5/1972 | Nelson | 435/296 |
| 3,749,646 | 7/1973 | Pirt | 435/296 |
| 3,814,585 | 6/1974 | Bailly | 23/230 B |
| 3,918,908 | 11/1975 | Moyer et al. | 23/230 B |
| 4,604,894 | 8/1986 | Kratzer et al. | 73/64.1 |
| 5,039,617 | 8/1991 | McDonald et al. | 436/69 |
| 5,047,211 | 9/1991 | Sloane, Jr. et al. | 422/73 |
| 5,089,422 | 2/1991 | Brubaker | 436/69 |

FOREIGN PATENT DOCUMENTS

| | | | |
|---|---|---|---|
| 1129425 | 6/1984 | European Pat. Off. | 33/48 |
| 87/00633 | 3/1988 | WIPO | 33/49 |
| 91/00438 | 10/1991 | WIPO | 33/49 |

OTHER PUBLICATIONS

D. B. Brubaker, *An In Vitro Bleeding Time Test*; Am. Jnl. of Clinical Path., vol. 91, No. 4, Apr. 1989 pp. 422–429.

Primary Examiner—William H. Beisner
Attorney, Agent, or Firm—Wells, St. John, Roberts, Gregory & Matkin

[57] ABSTRACT

A low cost, disposable device for in vitro determination of bleeding time is detachably connectable to the end of a syringe. The device includes a hollow body having inlet and outlet ports and a detachable cover designed to hold a tissue-simulating membrane against the body. Openings are formed in the body and cover to expose the membrane to blood that is passed through the hollow body under pressure from the syringe. Blood flows through a slit in the membrane until it clots. Bleeding time is determined as the time elapsed before the blood stops flowing through the slit. A blood collection reservoir is provided about the body to collect blood discharged from the device to reduce health risks associated with handling blood.

28 Claims, 11 Drawing Sheets

FIG. 1

$\rightarrow | D_C | \leftarrow$

DEVICE FOR IN VITRO BLEEDING TIME DETERMINATION

TECHNICAL FIELD

This invention relates to devices for in vitro measurement of blood clotting, and particularly, to bleeding time determination.

BACKGROUND OF THE INVENTION

The bleeding time determination is an important test frequently performed before major surgery. The conventional bleeding test is performed "in vivo" (meaning, in the living body) by placing a blood pressure cuff at 40 mm Hg on a surgery patient's arm and cutting an incision of standard size into the arm. The time for the blood to form a clot, thereby stopping the flow of blood, is measured using a stop watch. Normal values are between one to six minutes. This wide range renders the test inaccurate and insensitive. Furthermore, the test necessarily causes pain and scars the patient's arm.

Blood clotting is a complicated physiological process that involves various proteins called coagulation factors, as well as cells called platelets. The platelets adhere and aggregate at the site of the wound for proper clotting. The bleeding time test measures the total effect of all the factors working in concert. Unfortunately, if the bleeding is prolonged, the in vivo test will not provide information to the clinician to isolate the deficiency which is causing the prolonged bleeding time. For example, the standard in vivo test cannot differentiate between platelets not adhering and the absence of a coagulation factor.

A blood vessel wall has several layers. The innermost layer, that which is in contact with the flowing blood, is made of endothelial cells. These cells prevent platelets from adhering. The outer layers are called the subendothelium, and contain collagen and other proteins which promote platelet adherence.

At the cut site, the vessel injury exposes collagen and other subendothelial proteins which promote platelet adhesion and aggregation. The strongest of these proteins is collagen. Collagen activates prokallikrein and this in turn initiates activation of an intrinsic coagulation pathway. There are a total of thirteen coagulation factors (F I-F XIII), where each activates the others. Platelets also interact with coagulation factors, mainly factors X, XI, and XII. Platelets release proteins from their granules, including one called platelet factor 3 (PF3) which acts as a procoagulant.

As platelets breakdown due to enzymes in granules, phopholipids on the internal side of the platelet membrane are exposed which enhances an extrinsic coagulation pathway. The thirteen different coagulation factors are divided between the intrinsic and extrinsic coagulation pathways. As more and more platelets adhere, an aggregation of platelets forms, plugging the hole in the vessel, and promoting the coagulation factors to form fibrin. That is, the end result of the two coagulation pathways is insoluble fibrin, a fibrous protein that interweaves between the aggregated platelets. The cut vessel also releases coagulation factors causing the vessel downstream of the cut to constrict.

There are two tests which measure the function of plasma coagulation factors. A first test measures the cascading extrinsic pathway and is known as the prothrombin time (abbreviated "PT"). A second test measures the intrinsic pathway and is called the partial thromboplastin time (abbreviated "PTT"). The PT and PTT tests are performed on every patient going to surgery. If one of these tests is abnormal, additional tests are conducted to look for a factor(s) deficiency. These are routine tests currently performed in the medical laboratory.

Platelet function studies are performed primarily by three routine methods: platelet aggregation, platelet adhesion, and in vivo bleeding time test. The platelet aggregation test is performed by the medical laboratory and utilizes platelet rich plasma separation from the patient's body. Aggregating agents (e.g., collagen, ADP, epinephrine, and ristocetin) are added. As the platelets aggregate, the optical density decreases with time. Aggregation studies are not exact and do not replicate the formation of a platelet plug at the site of a cut vessel.

The platelet adhesion test is measured by pushing blood through a plastic tube filled with tiny glass beads. The beads serve as foreign material to which the platelets adhere. The platelet count is measured prior to passing blood through the column and after leaving the column and reflects the percent platelets retained. Other sophisticated tests using monoclonal antibodies and chromogenic assays can also be used to measure specific membrane or granule proteins.

It would be advantageous to have an "in vitro" (meaning, outside of the living body) test that more accurately mimics what occurs at the site of a wound. Blood could be obtained by conventional blood gathering techniques and the bleeding time could then be conveniently measured without subjecting the patient to additional incisions.

U.S. Pat. No. 5,089,422, also to Dr. Daniel Brubaker, discloses an in vitro bleeding time determination apparatus. The apparatus includes a tubular device formed by heating, blowing, and stretching polyethylene tubing and a fabric membrane impregnated with clot-promoting proteins. The membrane is epoxyed onto a window in the tube. The tubular device proved effective in experimental tests, but the blown tube was not conductive to mass, low cost production. Additionally, the device experienced leakage around the epoxyed membrane. In some experimental series, the coefficient of variation was over 20%.

Another problem concerning the handling of blood is health safety. Blood samples may carry sexually transmitted infectious agents such as HIV 1 and 2, Hepatitis B, syphilis, etc. which could infect the clinician if proper safeguards are not in place.

This invention provides an in vitro bleeding time determination device that is suitable for low cost manufacturing. The device of this invention also promotes health safety in that the bleeding time tests can be conducted without handling the blood or without the risk of blood escaping the device to spill onto the clinician.

The in vitro testing device of this invention permits more standardized bleeding time tests than can be accomplished by the in vivo techniques. Variables such as depth of wound, length of wound, blood pressure of the patient, and location of the wound on the patient's body are all automatically compensated for since the test is independent of the patient's body. Bleeding time can therefore be isolated as the sole testing variable.

The device of this invention can further be used to systematically exclude specific blood clotting factors from the test, thereby testing each variable individually.

The PT and PTT tests can therefore be augmented, and perhaps replaced.

BRIEF DESCRIPTION OF THE DRAWINGS

One or more preferred forms of the invention are described herein with reference to the accompanying drawings. The same reference numerals are employed throughout the drawings to represent like components or features. The drawings are briefly described below.

DETAILED DESCRIPTION OF THE PREFERRED EMBODIMENTS

This disclosure of the invention is submitted in furtherance of the constitutional purposes of the U.S. patent Laws "to promote the progress of science and useful arts" (Article 1, Section 8).

This invention provides an inexpensive, disposable assembly used to conduct in vitro bleeding time tests, such as prothrombin time (PT) and partial thromboplastin time (PTT) tests. The assembly replicates an injured or cut blood vessel where a portion of the blood flows out through the cut and a portion of the blood continues through the vessel distal to the cut. In addition to PT and PTT tests, the assembly is used to measure clot formation, blood clotting times, and specific blood clotting factors (individually or in combination).

U.S. Pat. No. 5,089,422 describes an apparatus and method for in vitro bleeding time determination. This patent is incorporated herein by reference. This invention provides an improved, mass producible device that can be used in the apparatus described in this patent.

System

Figure 1:
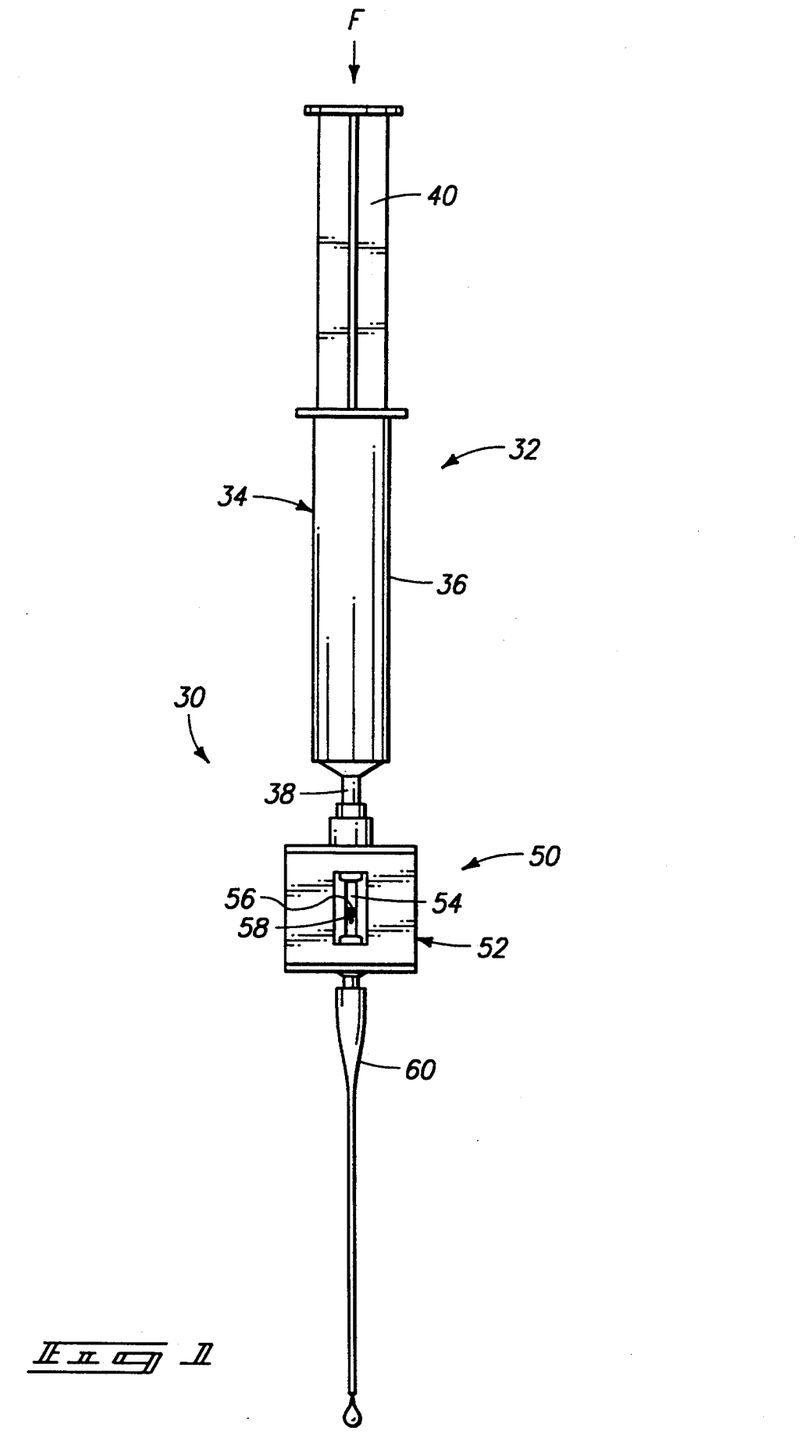
FIG. 1 shows an in vitro bleeding time determination system comprising a ruptured vessel simulating device attached to a pressure inducing syringe.
Figure 2:
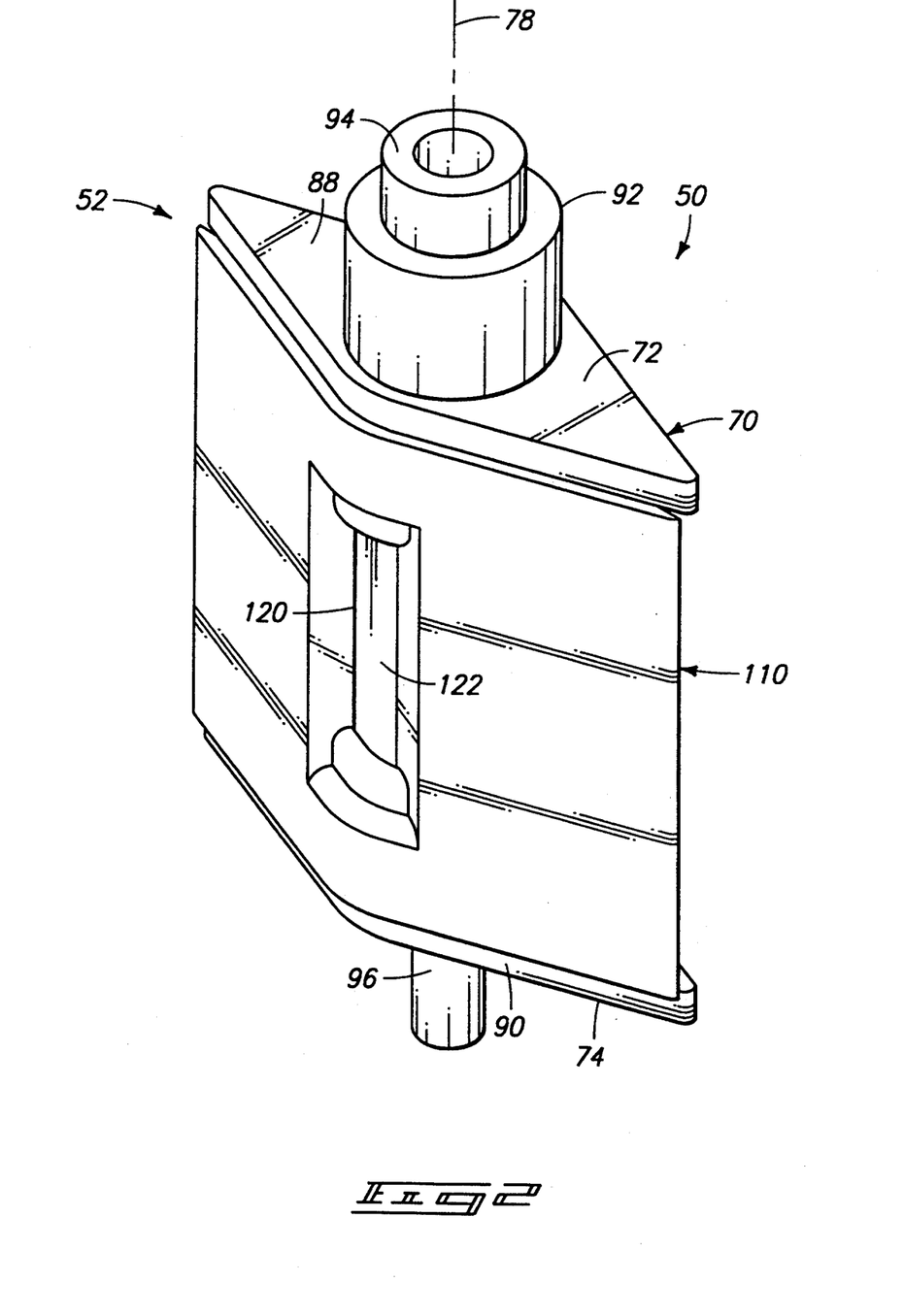
FIG. 2 is an isometric view of the vessel simulating device.

FIG. 1 shows an in vitro bleeding time determination system 30 according to this invention. System 30 has a blood pressurizing mechanism 32 in the form of a standard syringe 34. Syringe 34 includes an elongated tube 36 for holding a supply of blood, a discharging end 38, and a plunger 40 for displacing the blood from the tube 36 out through discharging end 38 under a force F. Syringe 34 is preferably formed of plastic, although glass and other materials can be used. Plunger force F is preferably constant and effective to induce a pressure approximating the patient's blood pressure. Force F can be applied manually or via weights, but is preferably generated by an automatic syringe plunger depression mechanism (not shown).

Bleeding time determination system 30 also has a ruptured vessel simulating device 50 that is detachably connectable to discharging end 38 of pressure syringe 34. Ruptured vessel simulating device 50 replicates an injured or cut blood vessel. In the human body, when a vessel is cut, platelets adhere and aggregate to the cut site. Fibrin forms and red and white blood cells are entrapped to produce a clot at the cut site. Simultaneously, the portion of the vessel distal to the cut site gradually constricts to force more blood (and hence, more platelets) at higher shear rates through the cut tissue. The increased shear rates cause platelets to stick and aggregate at the cut site.

Vessel simulating device 50 replicates these natural phenomena. Device 50 comprises a membrane holding assembly 52 which holds a tissue-simulating membrane 54. As blood discharged from the syringe is passed under force through device 50, membrane 54 acts as a vessel wall that is in contact with the flow of blood. Tissue-simulating membrane 54 is coated with a material for promoting blood clotting. A horizontal slit 56 is made in membrane 54 to simulate a cut or injury in a vessel wall. Blood seeps through the slit as pictorially represented by seepage 58. Device 50 also comprises a constricting tube 60 connected below and downstream from cut 56 to simulate a distal constricted blood vessel.

To measure bleeding time using system 30, blood is displaced through ruptured vessel simulating device 50 under force F from syringe 34. Blood flows through both the horizontal membrane slit 56 and the constricted tube 60. The blood clotting material on the membrane interacts with the blood to form a clot over time at the slit location. The bleeding time can be calculated in several ways, including monitoring when seepage through the membrane slit stops, when blood flow through distal tube 60 reaches study state, or when the rate at which the plunger 40 falls becomes constant.

Ruptured Vessel Simulating Device

FIGS. 2–10 illustrate ruptured vessel simulating device 50 in more detail. Device 50 includes a body 70 and a detachable membrane cover 110 which detachably connects to body 70 to hold tissue-simulating membrane 54 in place against the body. In this manner, body 70 and membrane cover 110 form membrane holding assembly 52. Adhesive may also be used to assist in holding membrane 54 in its appropriate location. Additionally, the entire membrane holding assembly 52 can be bonded together, for example, with triethylene chloride. Body 70 and cover 110 are preferably formed of plastic, and more particularly, of polycarbonate, which does not promote blood clotting.

Body 70 is described in more detail with reference to FIGS. 2–15. Body 70 has a first, proximal upper end 72 and a second, distal lower end 74. Body 70 is hollow and thereby defines a cylindrical-shaped body cavity or chamber 76 (FIG. 6) which extends vertically along longitudinal axis 78 between the upper and lower ends 72, 74.

Figure 6:
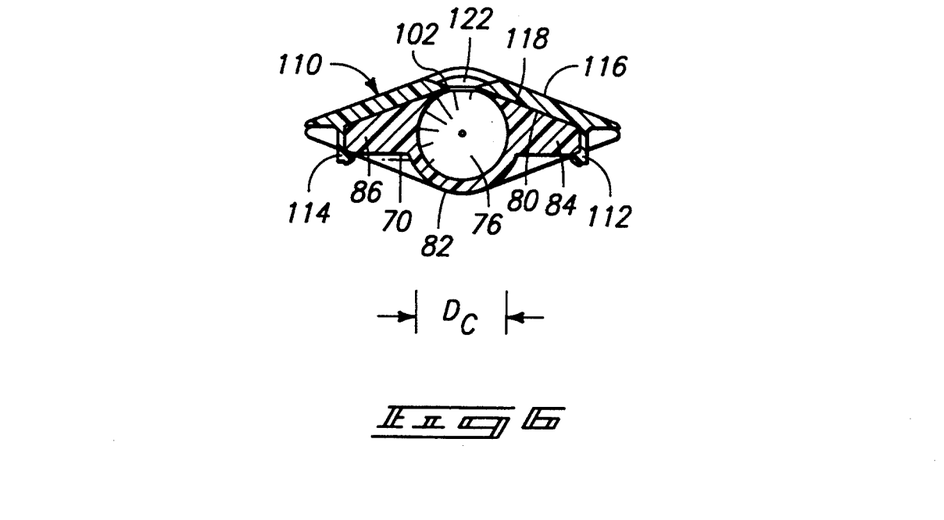
FIG. 6 is a cross-sectional view taken along line 6—6 in FIG. 5.
Figure 12:
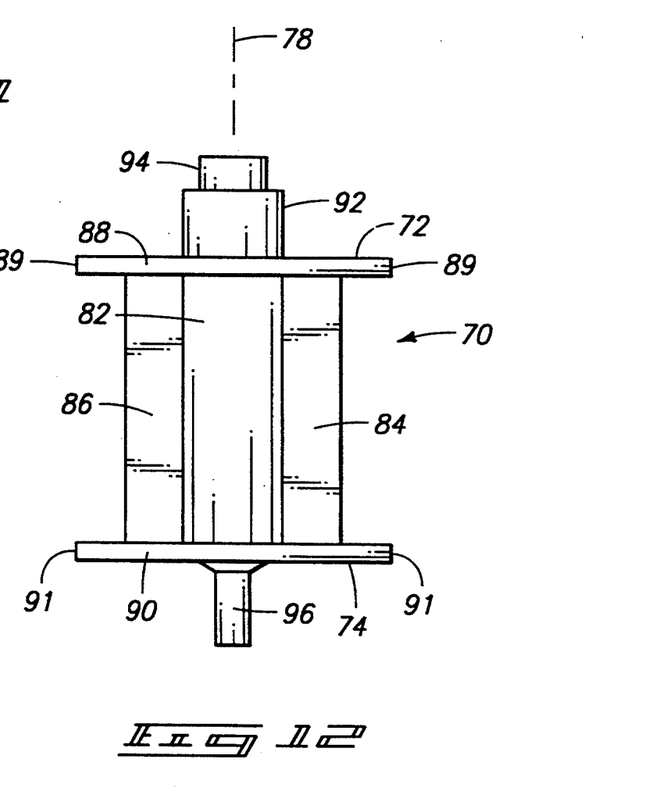
FIG. 12 is a back view of the body.
Figure 13:
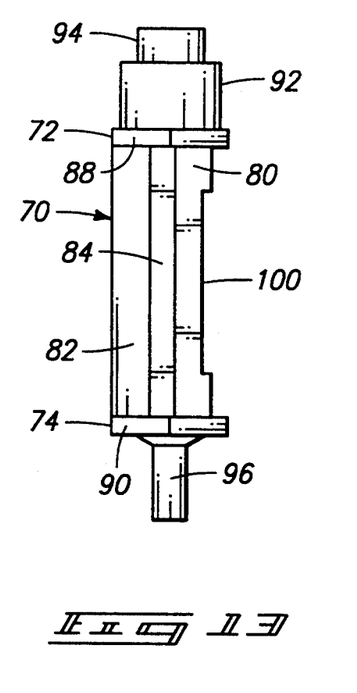
FIG. 13 is a side view of the body.
Figure 14:
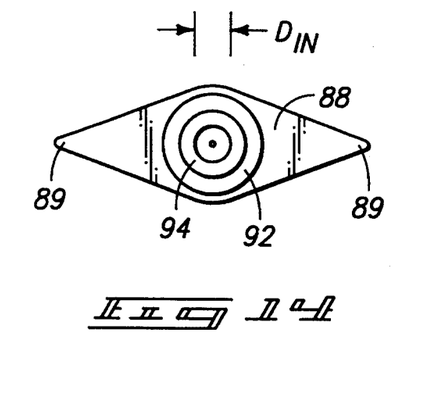
FIG. 14 is a top view of the body.
Figure 15:
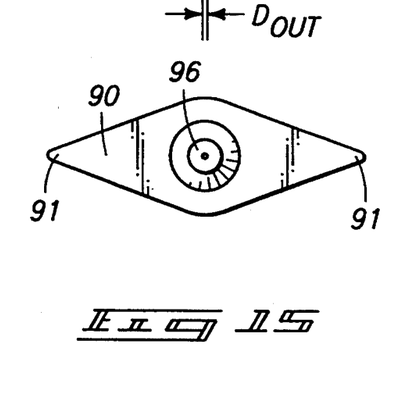
FIG. 15 is a bottom view of the body.
Figure 16:
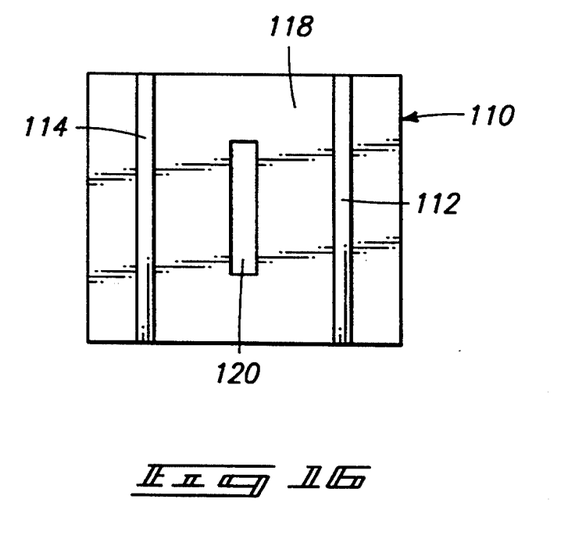
FIG. 16 is a front view of the FIG. 3 membrane cover of the vessel simulating device.
Figure 17:
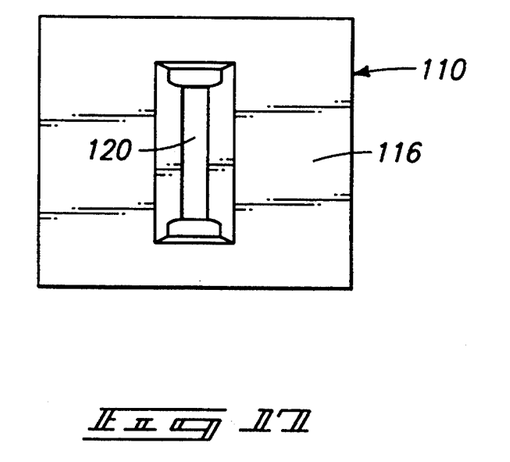
FIG. 17 is a back view of the membrane cover.
Figure 18:
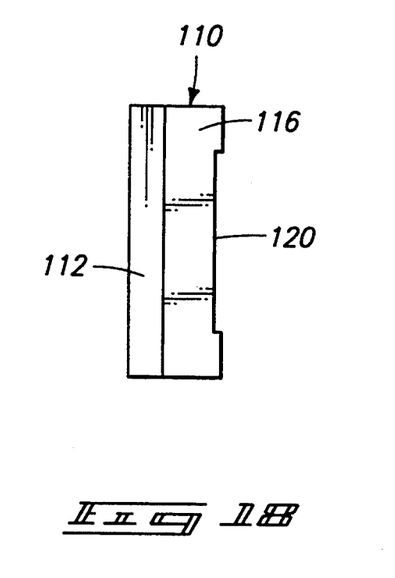
FIG. 18 is a side view of the membrane cover.
Figure 19:
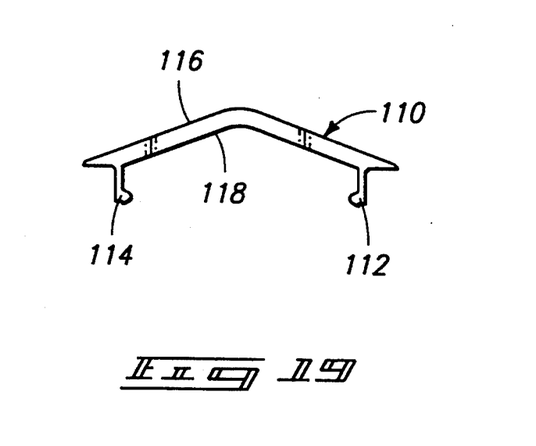
FIG. 19 is a top view of the membrane cover.

Body 70 has a V-shaped front side wall 80 (FIGS. 3, 6, and 11) and an cylindrical-shaped back side wall 82 (FIGS. 6 and 12). Front wall 80 extends outwardly from axis 78 to form opposing flanges 84 and 86 which are used to secure membrane cover 110 to the body. Body 70 also has a top platform 88 at the upper end 72 and bottom platform 90 at the lower end 74. The top and bottom platforms 88, 90 are diamond-shaped parallelograms (FIGS. 2, 14, and 15) which have opposing tips 89 and 91, respectively, that project beyond body flanges 84 and 86.

Figure 7:
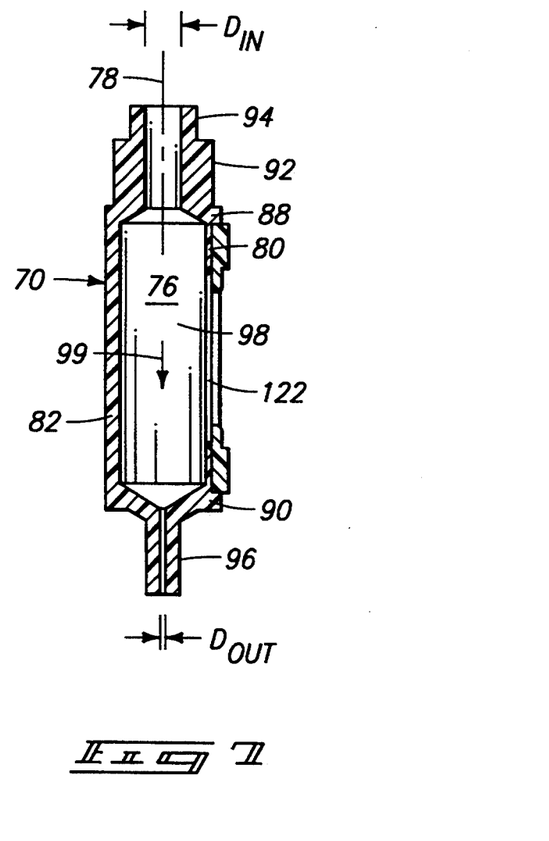
FIG. 7 is a cross-sectional view taken along line 7—7 in FIG. 4.
Figure 8:
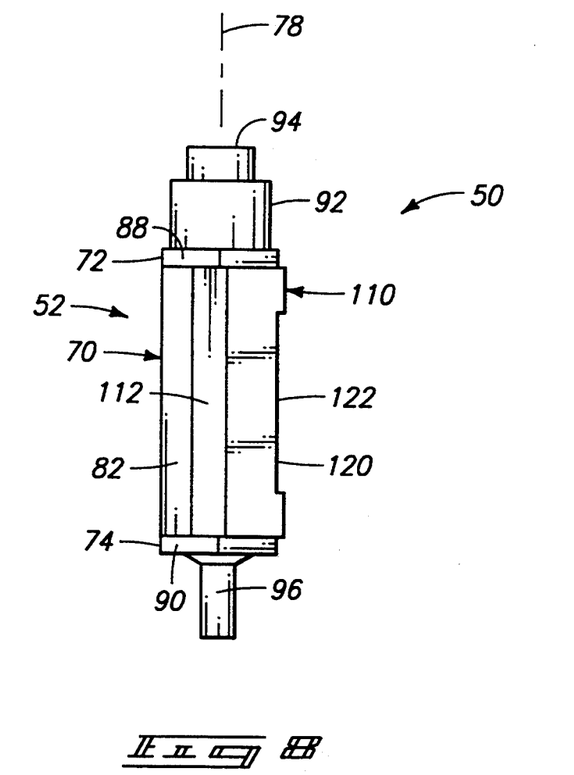
FIG. 8 is a side view of the vessel simulating device.
Figure 9:
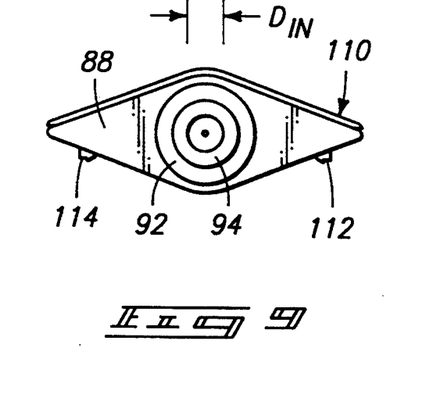
FIG. 9 is a top view of the vessel simulating device.

Ruptured vessel simulating device 50 has a blood receiving inlet port 92 provided at the body upper end 72 adjacent to top platform 88. Inlet port 92 is preferably cylindrical shaped and extends along longitudinal axis 78. Inlet port 92 defines a proximal aperture in fluid communication with chamber 76 of body 70 to permit blood to flow into the chamber. As shown in FIGS. 7 and 9, inlet port 92 has an inner diameter $D_{IN}$ which defines a first cross-sectional area. Inlet port 92 also forms in part a detachable coupling collar 94 that is sized to sealingly attach to the discharging end 38 of syringe 34 (FIG. 1). Coupling collar 94 is preferably a friction mount which slides onto syringe end 38, but can also include threaded or other coupling arrangements.

Figure 10:
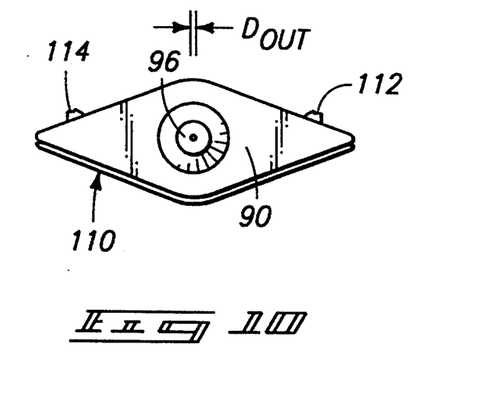
FIG. 10 is a bottom view of the vessel simulating device.
Figure 11:
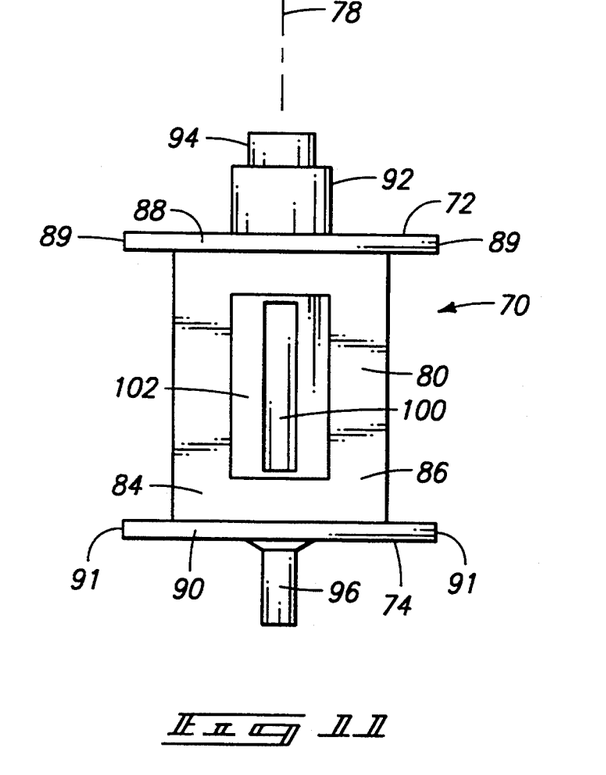
FIG. 11 is a front view of the FIG. 3 body of the vessel simulating device.

A blood discharging outlet port 96 is provided at the body lower end 74 adjacent to bottom platform 90. Outlet port 96 is preferably cylindrical shaped and extends along longitudinal axis 78. Outlet port 96 defines a distal aperture in fluid communication with chamber 76 of body 70 to permit blood to flow out from the chamber. As shown in FIGS. 7 and 10, outlet port 96 has an inner diameter $D_{OUT}$ of approximately 0.1–0.2 centimeter.

It is noted that outlet port 96 has a second cross-sectional area that is less than the first cross-sectional area of inlet port 92. This smaller sized outlet port helps to simulate the natural phenomenon of the constricting blood vessel distal to the cut site. Additionally, chamber 76 has a diameter $D_C$ (FIG. 6) which is at least equal to, and can be slightly larger than, the diameter $D_{IN}$ of inlet port. Alternatively, chamber 76 can taper from inlet port 92 to outlet port 96 to form a conical cavity, or as another example, taper from a location just below the body opening toward the outlet port.

Inlet port 92, chamber 76, and outlet port 96 define a communicating fluid passageway 98 (FIG. 7) that extends approximately vertically along longitudinal axis 78 between the upper and lower ends. Blood flows downward through vertical fluid passageway 98 from inlet port 92, through body cavity 76, to outlet port 96 as indicated by arrow 99.

Figure 3:
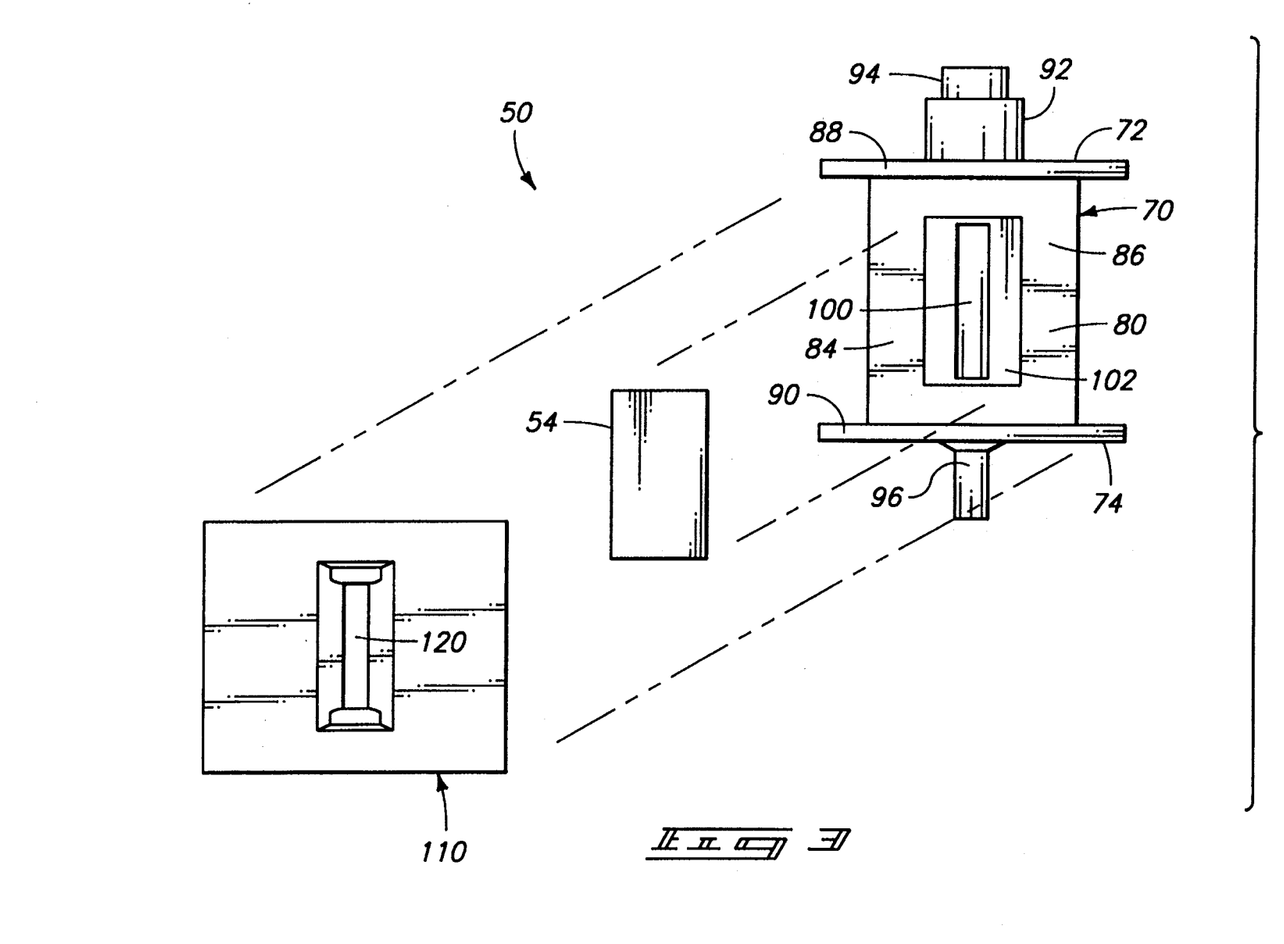
FIG. 3 is an exploded front view of the vessel simulating device showing a body, a tissue-simulating membrane, and a membrane cover.
Figure 4:
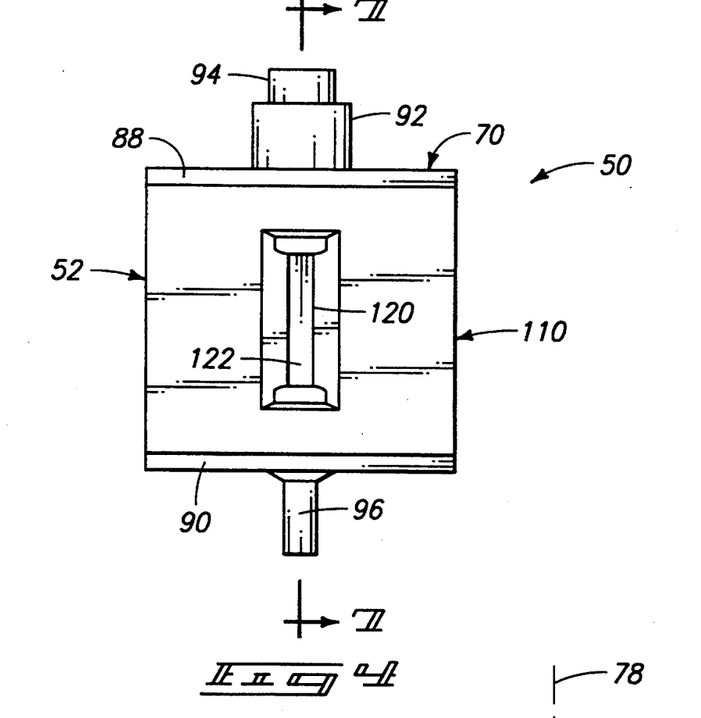
FIG. 4 is a front view of the vessel simulating device.

A body opening 100 is formed in front side wall 80 of body 70. Body opening 100 is a rectangular aperture elongated relative to axis 78 and opens into fluid passageway 98. Body opening 100 is preferably 0.2–0.3 centimeters wide and about 0.8 centimeters long. A recessed mounting area 102 is indented in front side wall 80 (FIGS. 3, 6, and 11) surrounding opening 100 to accommodate the clot promoting membrane 54 (FIG. 3). Membrane 54 stretches across opening 100, and can be adhesively secured at its outer edges to recess mounting area 102 via an appropriate adhesive that does not interact with the clot promoting proteins coated on the membrane. A horizontal incision 56 (FIG. 1) is made in membrane 54 such that when the slit membrane is mounted over opening 100, the slit is transverse to vertical fluid passageway 98 (FIG. 7). During operation, blood passes under pressure along fluid passageway 98 and out from chamber 76 simultaneously through opening 100 and the membrane slit 56.

Figure 5:
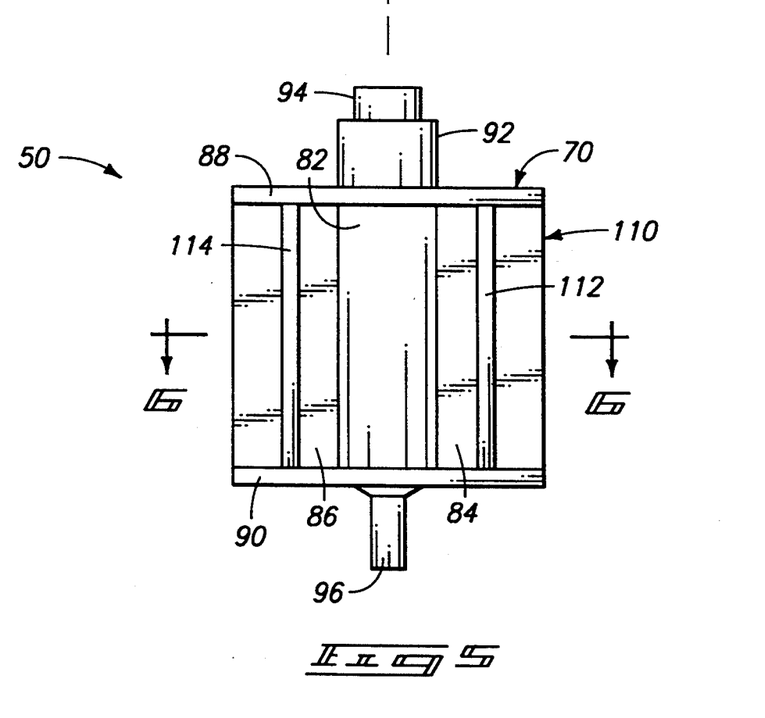
FIG. 5 is a back view of the vessel simulating device.

Membrane cover 110 of vessel simulating device 50 is described in more detail with reference to FIGS. 2–10 and 16–19. Membrane cover 110 is designed to attach to body 70 and thereby hold membrane 54 against body 70 and over body opening 100. In the preferred embodiment, cover 110 has two deflectable clips 112 and 114 which releasibly snap onto respective flanges 84 and 86 of body 70 (FIGS. 5 and 6).

Detachable membrane cover 110 has a V-shape that conforms to the contour of front side wall 80 of body 70. Cover 110 has an outside surface 116 and an inside surface 118. When the cover is attached to the body, insider surface 118 abuts front side wall 80. Membrane 54 is held in recessed mounting area 102 by being sandwiched between inside surface 118 of cover 110 and front side wall 80 of body 70.

A cover opening 120 is formed in the center of membrane cover 110. Cover opening 120 is a rectangular aperture elongated relative to longitudinal axis 78 and is approximately the same size of body opening 100 (i.e., 0.2–0.3×0.8 centimeters), although it can be other sizes and shapes. When membrane cover 110 is attached to body 70, cover opening 120 is aligned with body opening 100 to form a single window 122 to chamber 76. The tissue-simulating membrane 54, when mounted in the membrane holding assembly 52, is held suspended within window 122 in contact with the blood passageway 98 to thereby simulate a side wall of a blood vessel.

To prepare the ruptured vessel simulating device 50 for use in bleeding time tests, membrane cover 110 is first detached from body 70. A tissue-simulating membrane 54 is prepared (in the manner described below) and laid within recessed mounting area 102 over body opening 100. Membrane cover 110 is then reattached to body 70 atop membrane 54 to hold the membrane against the body. The entire assembly is then bonded with triethylene chloride. The bonding adhesive has no effect on the proteins in and on the membrane. A slit and/or hole are made in the membrane suspended in window 122 utilizing an 18 gauge needle. The ruptured vessel simulating device 50 is then ready for connection to a syringe or other blood pressurizing mechanism to begin blood clotting measurements.

Figure 20:
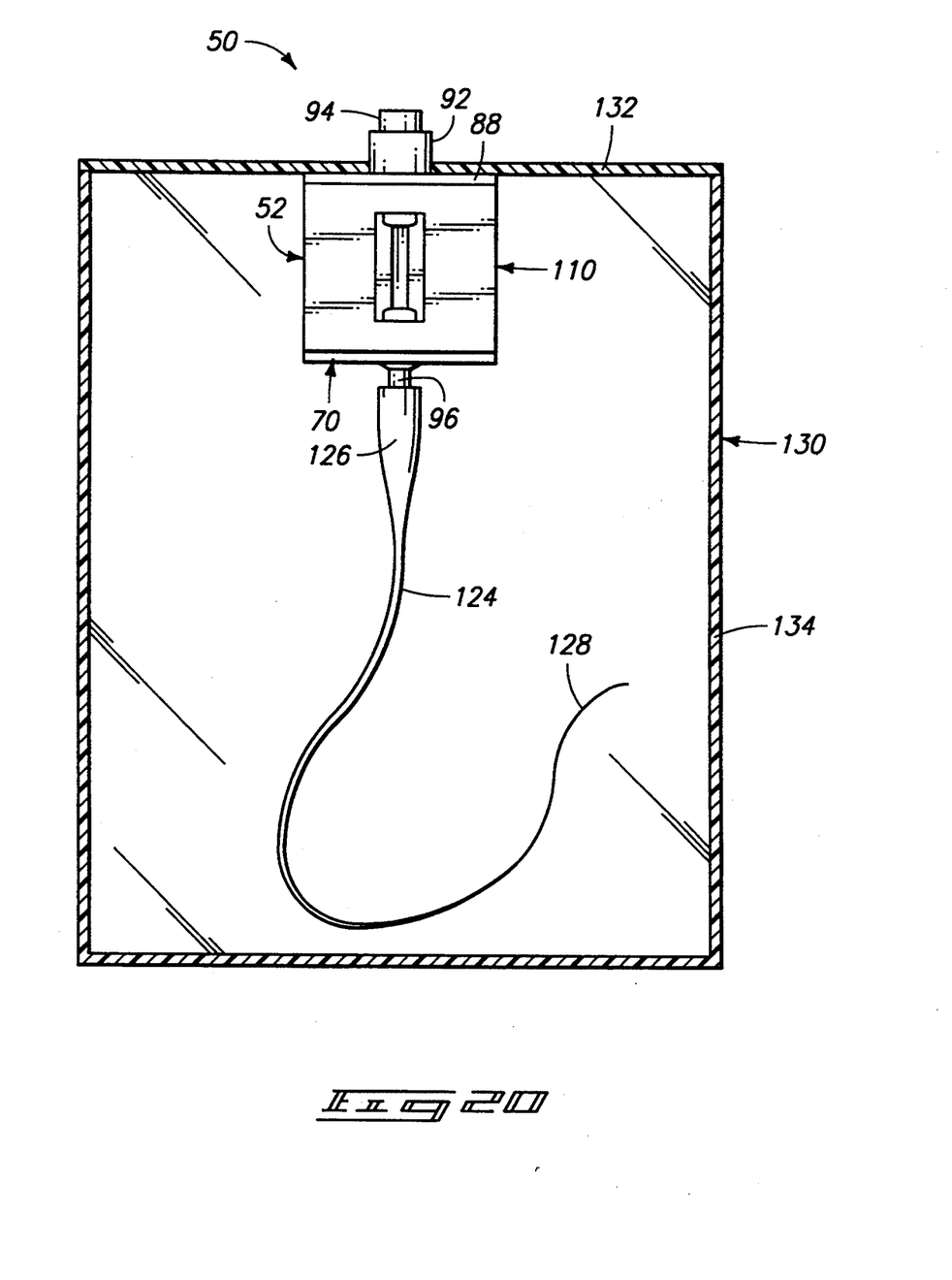
FIG. 20 is a partial cross-sectional view illustrating the vessel simulating device housed within a blood collection reservoir.

FIG. 20 shows an elongated constricting tube 124 coupled to outlet port 96. Tube 124 defines a continuously constricting fluid channel that is in fluid communication with outlet port 96 and blood passageway 98 so that blood flowing through body 70 can exit through lower end port 96 and tube 124. More particularly, tube 124 has a cross-sectional area that decreases from a proximal end 126 connected to outlet port 96 to a distal end 128. The inner diameter at distal end 128 is preferably 100–500 microns. Tube 124 is preferably twelve inches in length. Tube 124 thereby simulates a constricted blood vessel distal to the cut site. The constricting tube slows blood flow distal to the cut membrane, thereby causing more blood to flow through the slit to facilitate blood clotting.

FIG. 20 also shows ruptured vessel simulating device 50 housed within a blood collection reservoir 130. Reservoir 130 has a lid 132 that is attached to top platform 88 of body 70 and/or inlet port 92. Reservoir 130 has a container 134 that encompasses body 70 and outlet port 96. Lid 132 is connected to container 134 to form an entirely enclosed reservoir. When assembled, reservoir 130 collects blood that flows through (a) window 122 formed by body opening 100 and cover opening 120 and (b) outlet port 96 and tube 124. Reservoir 130 is preferably formed of clear plastic so that the clinician or health care provider can view the apparatus during the bleeding time tests. Other clear materials, such as glass, can also be used.

This invention therefore provides an inexpensive testing device for in vitro determination of bleeding time. Once the device is used for one or more tests of a patient's blood, it can simply be detached from the syringe or other blood pressurizing mechanism and then discarded. The disposable device is safe and lowers the health risks associated with handling potentially infectious blood in that the blood discharged from the vessel simulating device is completely captured within the enclosed reservoir. There is no human contact with the tainted blood, making the experimentation and disposal processes efficient and safe.

Tissue-Simulating Membrane

Tissue-simulating membrane 54 is designed to represent human tissue and the various proteins and other matter found therein. In the preferred form, membrane 54 comprises two rectangular porous filter layers placed together. An example size of the rectangular filters is approximately 0.8×1.5 centimeters. Individual filters are formed of nylon mesh and have a pore size ranging from 10–100 microns. One nylon mesh is coated with collagen, and more preferably with a composite of collagen, I-cyclohexl-3-(2-morpholinoethyl)-carbondiimide metho-p-toluenesulfonate (hereinafter "CDI"), and cryoprecipitate. The other nylon mesh remains untreated. The collagen coated layer of the membrane is turned inward toward the blood passageway 98 when held in membrane holder assembly 52.

One technique for preparing the tissue-simulating membrane is as follows. Two rectangular pieces of nylon mesh are cut to the desired dimensions to overlay the body opening. One mesh is coated on one side with Type I collagen. Type I collagen is insoluble and is usually prepared from Bovine Achilles Tendon.

A CDI solution is made having 1.5–6.0 mg CDI/ml of saline. The first nylon mesh is saturated in the CDI solution. Type I collagen powder is spread on top of the mesh. The Type I collagen becomes more soluble in CDI.

A Type III collagen solution is made having 5 mg/ml of saline. Type III collagen is an acid soluble from Calf Skin (Type I). The first nylon mesh is saturated with the Type III collagen, and is then dried at room temperature from 1.5 to 3 hours depending upon the wetness of the mesh from the collagen solutions.

The collagen coated nylon mesh is then saturated with a solution of Calcium Chloride (10 mg $CaCl_2$ ml of saline). A cryoprecipitate is prepared from frozen plasma, having concentrated fibrinogen (250–900 mg %), fibronectin (1–3 mg/ml), von Willebrandt's factor (10–60 mg/ml) and to a lesser degree, other coagulation factors. The cryoprecipitate is tested for sexually transmitted infectious agents such as HIV 1 and 2, Hepatitis B, syphilis, etc. and meets all the requirements by the FDA and the American Association of Blood Banks. The cryoprecipitate is added to completely coat the mesh.

The second, untreated mesh is then laid on top of the collagen-cryoprecipitate-coated mesh. The composite mesh is immediately placed in a 37 degree Celsius dry heat incubator to accelerate clotting and left overnight (about 12 hours).

The double mesh is removed from the incubator and a solution of 5 mg CDI/ml, cryoprecipitate, 5 mg Type III Collagen per ml saline and Collagen Type I is layered on top of the membrane. The membrane is then allowed to dry at a temperature between room temperature (i.e., 20–25 degrees Celsius) and refrigerator temperature (i.e., 4–6 degrees Celsius). Thereafter, the double mesh membranes can be stored indefinitely at room temperature.

In compliance with the statute, the invention has been described in language necessarily limited in its ability to properly convey the conceptual nature of the invention. Because of this inherent limitation of language, it must be understood that the invention is not necessarily limited to the specific features described, since the means herein disclosed comprise merely preferred forms of putting the invention into effect. The invention is, therefore, claimed in any of its forms or modifications within the proper scope of the appended claims appropriately interpreted in accordance with the doctrine of equivalents.

We claim:

1. A ruptured vessel simulating device comprising:
   a body; the body defining a chamber;
   a blood receiving inlet port to the body in fluid communication with the chamber; the inlet port permitting blood to flow into the chamber;
   a blood discharging outlet port to the body in fluid communication with the chamber; the outlet port permitting blood to flow out from the chamber;
   the inlet port, chamber, and outlet port defining a communicating fluid passageway;
   a body opening formed in the body along the fluid passageway; the body opening permitting a portion of blood to flow out from the chamber; and
   a detachable membrane cover detachably connectable to the body configured for holding a tissue-simulating membrane over the body opening.

2. A ruptured vessel simulating device according to claim 1 wherein the inlet port has a larger cross-sectional area than that of the outlet port.

3. A ruptured vessel simulating device according to claim 1 wherein the inlet port forms in part a detachable coupling collar sized to be sealingly attachable to a syringe.

4. A ruptured vessel simulating device according to claim 1 wherein the inlet and outlet ports are on opposite ends of the body.

5. A ruptured vessel simulating device according to claim 1 wherein:
   the body has an upper end and a lower end;
   the inlet port is provided at the upper end of the body;
   the outlet port is provided at the lower end of the body; and
   the body opening is formed in the body between the upper and lower ends.

6. A ruptured vessel simulating device according to claim 1 wherein:
   the body has at least one side wall extending between the inlet and outlet ports; and
   the body opening is formed in the side wall.

7. A ruptured vessel simulating device according to claim 1 wherein the membrane cover has deflectable clips which releasibly snap onto the body to attach the membrane cover to the body.

8. A ruptured vessel simulating device according to claim I wherein the body, inlet port, and outlet port are formed of a material which does not promote blood clotting.

9. A ruptured vessel simulating device according to claim 1 further comprising a cover opening formed in the membrane cover; the cover opening being aligned with the body opening when the membrane cover is connected to the body.

10. A ruptured vessel simulating device according to claim 1 further comprising an elongated constricting tube connected in fluid communication with the outlet port; the tube having a proximal end connected to the outlet port and a distal end, the tube having a cross-sectional area that decreases from the proximal end to the distal end to simulate a constricted blood vessel.

11. A ruptured vessel simulating device according to claim 1 further comprising a blood collection reservoir encompassing the body and the outlet port to collect blood that flows through the body opening and the outlet port.

12. A ruptured vessel simulating device comprising:
a body having an upper end, a lower end, and at least one side wall extending between the upper and lower ends; the body defining a chamber;
a blood receiving inlet port provided at the upper end of the body in fluid communication with the chamber; the inlet port permitting blood to flow into the chamber, the inlet port having a first cross-sectional area;
the inlet port forming in part a detachable coupling collar sized to be sealingly attachable to a syringe;
a blood discharging outlet port to the body in fluid communication with the chamber; the outlet port permitting blood to flow out from the chamber, the outlet port having a second cross-sectional area less than the first cross-sectional area of the inlet port;
the inlet port, chamber, and outlet port defining a communicating fluid passageway vertically extending between the upper and lower ends of the body;
an elongated body opening formed in the side wall of the body along the fluid passageway; the body opening permitting a portion of blood to flow out from the chamber; and
a detachable membrane cover detachably connectable to the body configured for holding a tissue-simulating membrane over the body opening; the membrane cover having deflectable clips which releasibly snap onto the body to attach the membrane cover to the body; and
an elongated cover opening formed in the membrane cover, the cover opening being aligned with the body opening when the membrane cover is connected to the body.

13. A ruptured vessel simulating device according to claim 12 further comprising an elongated constricting tube connected in fluid communication with the outlet port; the tube having a proximal end connected to the outlet port and a distal end, the tube having a cross-sectional area that decreases from the proximal end to the distal end to simulate a constricted blood vessel.

14. A ruptured vessel simulating device according to claim 12 further comprising a blood collection reservoir encompassing the body and the outlet port to collect blood that flows through the body opening and the outlet port.

15. A ruptured vessel simulating device comprising:
a body; the body defining a chamber;
a blood receiving inlet port to the body in fluid communication with the chamber; the inlet port permitting blood to flow into the chamber;
a blood discharging outlet port to the body in fluid communication with the chamber; the outlet port permitting blood to flow out from the chamber;
the inlet port, chamber, and outlet port defining a communicating fluid passageway;
a body opening formed in the body along the fluid passageway; the body opening permitting a portion of blood to flow out from the chamber;
a tissue-simulating membrane provided over the body opening; the membrane having a material for promoting blood clotting coated thereon, the membrane having a slit formed therein to permit the escape of blood therethrough;
a detachable membrane cover detachably connectable to the body configured for holding the tissue-simulating membrane over the body opening; and
a cover opening formed in the membrane cover; the cover opening being aligned with the body opening when the membrane cover is connected to the body.

16. A ruptured vessel simulating device according to claim 15 wherein the tissue-simulating membrane comprises two porous filter layers, one of the filter layers being coated with collagen.

17. A ruptured vessel simulating device according to claim 15 wherein the tissue-simulating membrane comprises two porous filter layers, one of the filter layers being coated with a composite comprising collagen, CDI, and cryoprecipitate.

18. A ruptured vessel simulating device according to claim 15 wherein:
the fluid passageway through the body is approximately vertical between the inlet port and the outlet port; and
the slit formed in the tissue-simulating membrane is approximately horizontal, thereby being transverse to the fluid passageway.

19. A ruptured vessel simulating device according to claim 15 wherein the body, the tissue-simulating membrane, and the membrane cover are bonded with triethylene chloride.

20. An in vitro bleeding time determination system comprising:
(a) a syringe having a discharging end and a plunger for displacing blood through the discharging end under force;
(b) a ruptured vessel simulating device detachably connected to the discharging end of the syringe, the vessel simulating device comprising:
a body; the body defining a chamber;
a blood receiving inlet port to the body in fluid communication with the chamber; the inlet port permitting blood to flow into the chamber;
the inlet port forms in part a detachable coupling collar sized for sealing attachment to the discharging end of the syringe;
a blood discharging outlet port to the body in fluid communication with the chamber; the outlet port permitting blood to flow out from the chamber;

the inlet port, chamber, and outlet port defining a communicating fluid passageway through which blood passes under force from the syringe;

a body opening formed in the body along the fluid passageway; the body opening permitting a portion of blood to flow out from the chamber;

a detachable membrane cover detachably connectable to the body configured for holding a tissue-simulating membrane over the body opening; and a cover opening formed in the membrane cover; the cover opening being aligned with the body opening when the membrane cover is connected to the body;

the syringe forcing blood through fluid passageway of the ruptured vessel simulating device so that a portion of the blood flows out of the chamber through the body opening and a portion of the blood flows out through the outlet port, whereby bleeding time can be determined based upon the flow of blood through the body opening.

21. An in vitro bleeding time determination system according to claim 20 wherein the inlet port has a larger cross-sectional area than that of the outlet port.

22. An in vitro bleeding time determination system according to claim 20 wherein:

the body has an upper end and a lower end;

the inlet port is provided at the upper end of the body;

the outlet port is provided at the lower end of the body; and the body opening is formed in the body between the upper and lower ends.

23. An in vitro bleeding time determination system according to claim 20 wherein the membrane cover has deflectable clips which releasibly snap onto the body to attach the membrane cover to the body.

24. An in vitro bleeding time determination system according to claim 20 further comprising a tissue-simulating membrane; the membrane comprising a porous filter coated with collagen.

25. An in vitro bleeding time determination system according to claim 20 further comprising an elongated constricting tube connected in fluid communication with the outlet port; the tube having a proximal end connected to the outlet port and a distal end, the tube having a cross-sectional area that decreases from the proximal end to the distal end to simulate a constricted blood vessel.

26. An in vitro bleeding time determination system according to claim 20 further comprising a blood collection reservoir encompassing the body and the outlet port to collect blood that flows through the body opening and the outlet port.

27. A ruptured vessel simulating device comprising:

a body; the body defining a chamber;

a blood receiving inlet port to the body in fluid communication with the chamber; the inlet port permitting blood to flow into the chamber;

a blood discharging outlet port to the body in fluid communication with the chamber; the outlet port permitting blood to flow out from the chamber;

the inlet port, chamber, and outlet port defining a communicating fluid passageway;

a body opening formed in the body along the fluid passageway; the body opening permitting a portion of blood to flow out from the chamber;

a tissue-simulating membrane provided over the body opening; the membrane having two porous filter layers, one of the filter layers being coated with a composite comprising collagen, CDI, and cryoprecipitate, the membrane having a slit formed therein to permit the escape of blood therethrough;

a membrane cover connected to the body configured for holding the tissue-simulating membrane over the body opening; and a cover opening formed in the membrane cover; the cover opening being aligned with the body opening when the membrane cover is connected to the body.

28. A ruptured vessel simulating device according to claim 27 wherein the body, the tissue-simulating membrane, and the membrane cover are bonded with triethylene chloride.

* * * * *